(12) United States Patent
Li

(10) Patent No.: US 6,719,697 B2
(45) Date of Patent: Apr. 13, 2004

(54) ULTRASONIC QUANTIFICATION OF VALVULAR REGURGITANT BLOOD FLOW

(75) Inventor: Xiang-Ning Li, Mill Creek, WA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 118 days.

(21) Appl. No.: 09/794,528

(22) Filed: Feb. 27, 2001

(65) Prior Publication Data

US 2002/0151794 A1 Oct. 17, 2002

(51) Int. Cl.⁷ ................................................ A61B 8/12
(52) U.S. Cl. ........................ 600/454; 600/437; 600/455; 600/453; 600/465; 600/468
(58) Field of Search ................................. 600/437–472, 600/453, 454, 455, 465, 468

(56) References Cited

U.S. PATENT DOCUMENTS

| | | | | |
|---|---|---|---|---|
| 4,608,993 A | * | 9/1986 | Albert | 600/457 |
| 4,790,322 A | * | 12/1988 | Iinuma | 600/456 |
| 4,913,159 A | * | 4/1990 | Gardin et al. | 600/456 |
| 4,926,872 A | * | 5/1990 | Brock-Fisher et al. | 600/457 |
| 5,010,528 A | * | 4/1991 | Ohtsuki et al. | 367/90 |
| 5,105,816 A | * | 4/1992 | Shimura et al. | 600/454 |
| 5,425,365 A | * | 6/1995 | Iinuma | 600/441 |
| 5,551,434 A | * | 9/1996 | Iinuma | 600/455 |
| 5,622,174 A | * | 4/1997 | Yamazaki | 600/441 |
| 6,149,595 A | * | 11/2000 | Seitz et al. | 600/438 |

OTHER PUBLICATIONS

Bargiggia et al., "A New Method for Quantitation of Mitral Regurgitation Based on color Flow Doppler Imaging of Flow Convergence Proximal to Regurgitant Orifice," Circulation, vol. 84, No. 4, Oct. 1991, pp. 1481–1489.

Deng et al., "Determination of the MOst Appropriate Velocity Threshold for Applying Hemispheric Flow Convergence Equations to Calculate Flow Rate: Selected According to the Transorifice Pressure Gradient (Digital Computer Analysis of the Doppler Color Flow Convergence Region," Circulation, Vol 88, No. 4, Part 1, Oct. 1993, pp. 1699–1708.

Enriquez–Sarano et al., "Effective Mitral Regurgitant Orifice Area: Clinical Use and Pitfalls of the Proximal Insovelocity Surface Area Method," JACC, Vol 25, No. 3, Mar. 1, 1995, pp. 703–709.

Thomas, "How Leaky is that Matral Valve? (Simplified Doppler Methods to Measure Regurgitant Orifice Area," Circulation, Vol 95, No. 3, Feb. 4, 1997, pp. 548–550.

* cited by examiner

Primary Examiner—Dennis W. Ruhl
Assistant Examiner—William Jung
(74) Attorney, Agent, or Firm—W. Brinton Yorks, Jr.

(57) ABSTRACT

Valvular regurgitation is assessed by identifying a characteristic regurgitation jet in a colorflow image. An M-line is placed over the region of regurgitation and Doppler M-mode information is acquired from the flow convergence region adjacent the regurgitant orifice. The Doppler M-mode information, acquired at a higher acquisition rate than the colorflow frame rate, is used to produce a measure of the regurgitant flow rate and volume through the orifice. The flow rate can be used with velocity data acquired during the regurgitation event to produce a dynamic estimate of the size of the regurgitant valve orifice.

27 Claims, 4 Drawing Sheets

ULTRASONIC QUANTIFICATION OF VALVULAR REGURGITANT BLOOD FLOW

This invention relates to ultrasonic diagnostic imaging systems and, in particular, to ultrasonic diagnostic imaging systems which are capable of detecting and quantifying valvular regurgitant blood flow in the heart.

Valvular regurgitation is a serious and potentially life-threatening heart condition. The condition arises when a valve in the heart does not fully close during a particular phase of the heart cycle. Full valve closure is necessary for a complete build-up of the maximum heart chamber blood pressure developed by contraction of the heart. If a valve of the chamber does not close completely, a leak will occur and a jet of blood will escape as the heart contracts. This inefficient operation will cause the heart to expend more effort than it should, can lead to a reduced flow of blood through the body, and in many cases leads to open heart surgery to repair or replace the leaking valve.

Ultrasonic detection of valvular regurgitation has traditionally been done by looking for the above-mentioned jet of blood. Over the past fifteen years detection of the jet has been facilitated by colorflow Doppler, in which the high speed and turbulence of the small jet of blood can be detected by careful search for these abnormal local flow velocities near the leaking heart valve. More recently a diagnostic procedure known as the proximal iso-velocity surface area method (PISA) has been endorsed by the cardiology community. In this method the suspect valve and the region inside the heart chamber and proximal to the valve are imaged by colorflow Doppler imaging. At the time of occurrence of the jet a flow convergence region (FCR) is formed in the proximal region as blood flow velocities in the region instantaneously accelerate toward the regurgitant orifice. This flow pattern results in aliasing in the colorflow image as the flow velocities momentarily exceed the velocity range used for the colorflow image. A colorflow image at this moment is captured and frozen on the display screen. A measurement is then made of the velocity v at the first aliasing line of the FCR, and a measurement is made of the distance r from the aliasing line to the center of the valve orifice. These two measurement are then used to compute the flow rate through the orifice using the expression $Q_r = 2\pi r^2 v$.

Several difficulties arise when conducting this procedure. One is that the greatest accuracy is obtained when the jet is captured in the colorflow image at its very peak. The duration of the jet during a heart cycle can be only 300–450 milliseconds, however, while a typical colorflow frame rate may be in the range of 10–20 frames per second. Thus it is probable that the time of acquisition of one of the colorflow image frames will not be the same as the time that the jet is at its peak. The clinician can repeat the colorflow acquisition sequence for additional cardiac cycles, or can settle for the inaccuracy causes by making the measurements at other than the peak of the jet.

Another problem is that the center of the valve orifice is not easy to define in the colorflow image. The valve tissue produces large reflections of ultrasound and is moving rapidly as scanning takes place, and can appear as a bulky, blurred or indistinct mass in the image. Thus it is possible that the accuracy of the measurement r will be compromised by the inability to estimate the exact location of the orifice.

Yet a third problem is that the PISA method is tedious and exacting, limiting its utility for routine use to measure regurgitant volumes in a clinical setting. The PISA method requires the clinician to make multiple measurements on each image frame of multiple image frames acquired during the regurgitation period of a heart cycle.

It is thus desirable to be able to measure the flow rate and volume at the regurgitant valve without such sources of inaccuracy and inconvenience.

In accordance with the principles of the present invention an ultrasonic system and technique are described for quantifying valvular regurgitant flow rate and volume. In one embodiment of the inventive technique the regurgitant valve is imaged by colorflow imaging. An M-line is positioned over the valve in the image by referencing the position of the jet, the FCR, and/or the approximate location of the orifice. A sequence of color M-mode measurements is then captured along the M-line. The time-sampled FCR during a cardiac cycle is defined in the color M-mode display by its distinctive aliasing color, and the distance across the FCR and velocities at each end of the distance are recorded. The instantaneous flow rate is then calculated from these measurements, and the volume flow during regurgitation is calculated as an integral of the instantaneous flow rates for all the regurgitant M-lines of a cardiac cycle. Since the sample rate of the M-lines can be one or two orders of magnitude greater than the colorflow frame rate, the peak of the jet can be reliably captured, and the inventive technique does not require any precise definition of the orifice location. Moreover, only one image, the color M-mode image, is needed for the diagnosis of a complete heart cycle.

Figure 1:
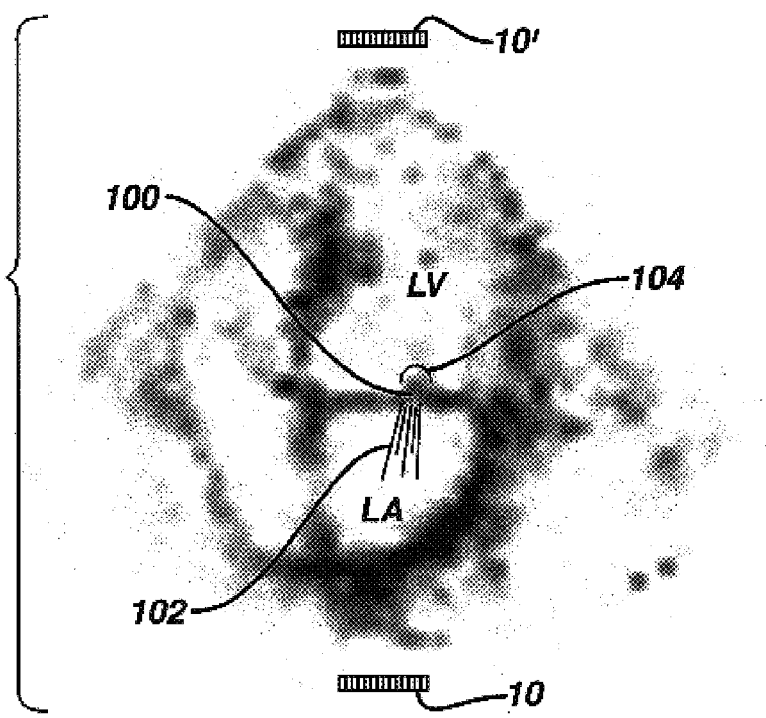
FIG. 1 illustrates a four chamber view of the heart.

Referring to FIG. 1, a four-chamber ultrasound image of the heart is shown in reverse grayscale. The ultrasound image of FIG. 1 was acquired transthoracically by an ultrasound probe 10' proximal to the apex of the heart. In a preferred embodiment the heart is imaged by a transesophageal echocardiography (TEE) transducer 10 located in the esophagus, which affords high quality images of the heart chambers and valves. An embodiment of the present invention may be used to measure regurgitant flow of either aortic or mitral heart valves. The embodiment illustrated in the drawing shows mitral regurgitation being measured, as mitral regurgitation is more prevalent than aortic regurgitation and is usually more susceptible to treatment. Shown in the image of FIG. 1 is the left ventricle (LV) and the left atrium (LA), separated by the mitral valve 100. Also depicted in the image is a jet 102 which would be characteristic of regurgitation by the mitral valve 100. In the past, clinicians would look for the telltale jet 102 as an indication of mitral regurgitation, then infer the size of the leaking valve orifice from the size and shape of the jet 102. In the illustration of FIG. 1 the jet is shown centered in the LA. However, the orifice of a leaking valve can be eccentrically located so that the jet can be proximal to or directed toward a wall of the atrial chamber. In that case, little about the orifice can be inferred from the eccentric jet, a situation in which the present inventive technique can be performed without degradation.

Figure 2:
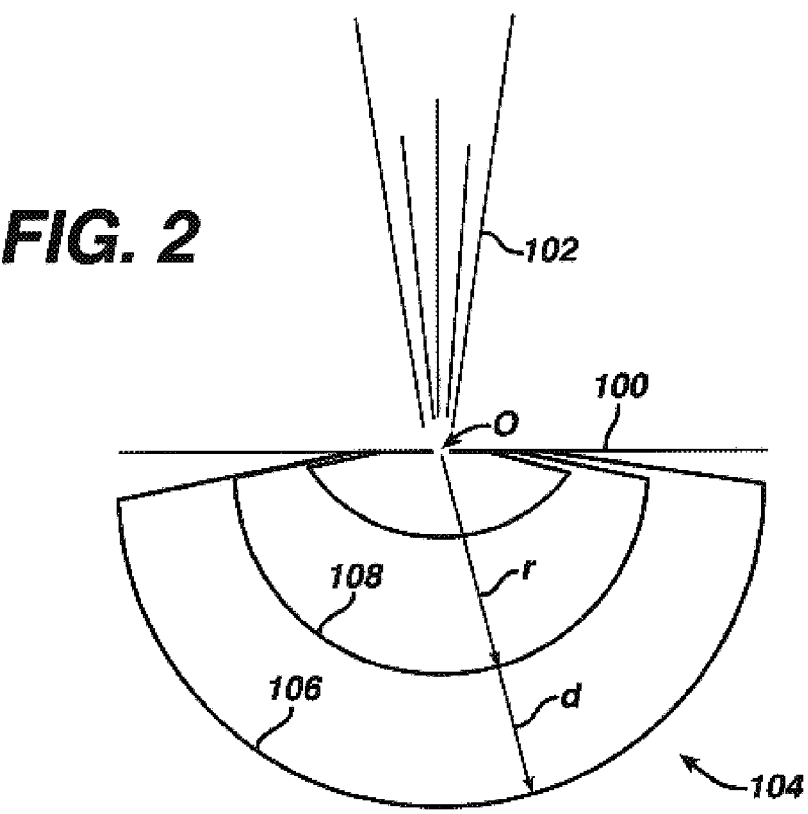
FIG. 2 is a schematic representation of a mitral valve and regurgitant jet.

Located in the LV proximal the orifice of the mitral valve is a region 104 of flow convergence (FCR). The flow convergence region 104 and the jet 102 are shown schematically in FIG. 2. The jet 102 is seen emanating from an orifice O in the mitral valve 100. Below the orifice O and the mitral valve plane is the FCR 104. When the FCR is imaged as explained below it will exhibit at least two iso-velocity lines 106 and 108 where local blood flow velocities exceed the chosen range of colorflow velocities. The iso-velocity lines are located in a colorflow image by looking for color change boundaries. The outermost iso-velocity line 106 marks a constant velocity boundary radiating approximately spherically around the orifice O, and is located a radial distance of r+d from the orifice. The next iso-velocity line 108 also marks a constant velocity boundary and is located a radial distance of r from the orifice.

Figure 3:
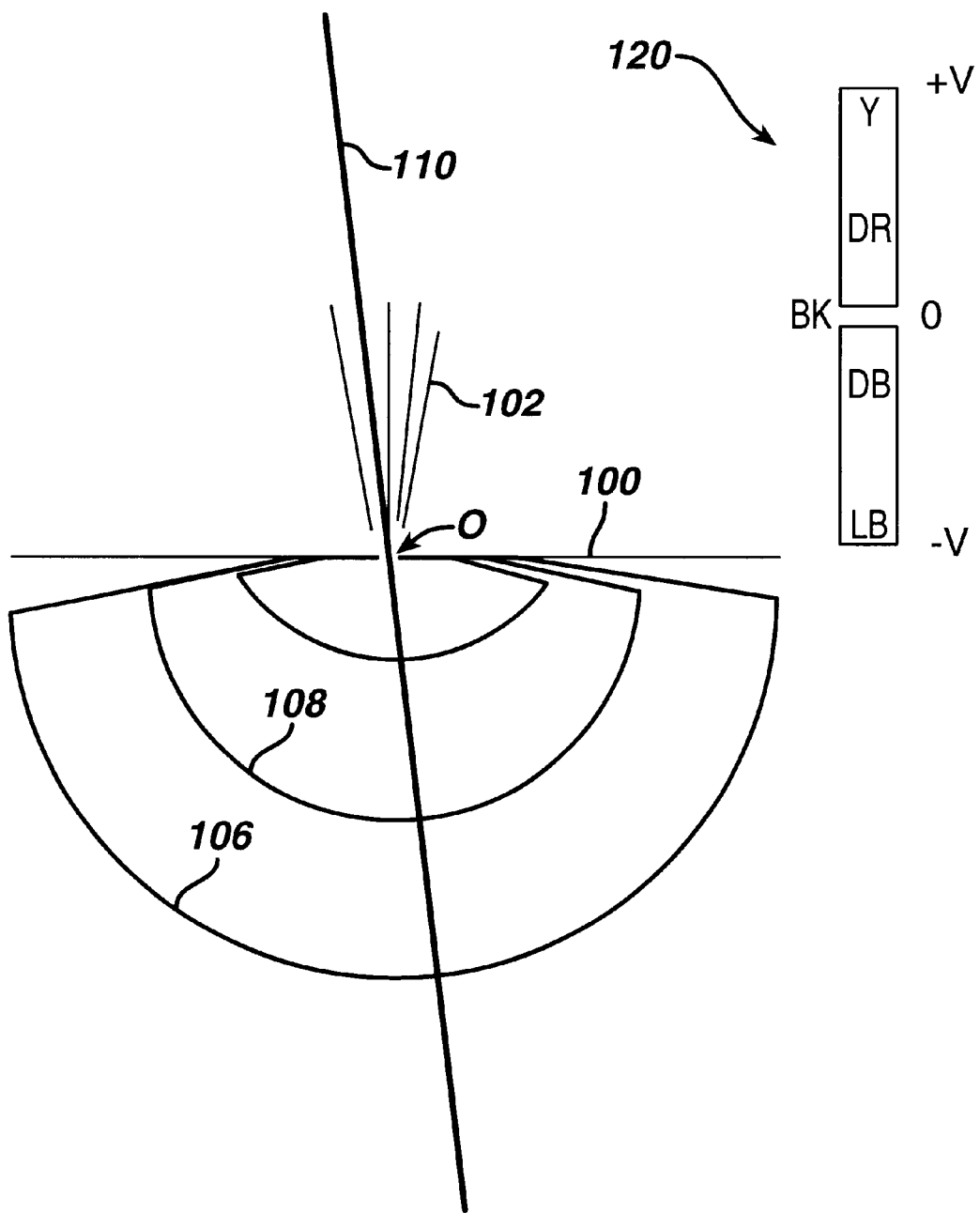
FIG. 3 is a schematic representation of a mitral valve and regurgitant jet with an M-line placed over the jet.
Figure 4:
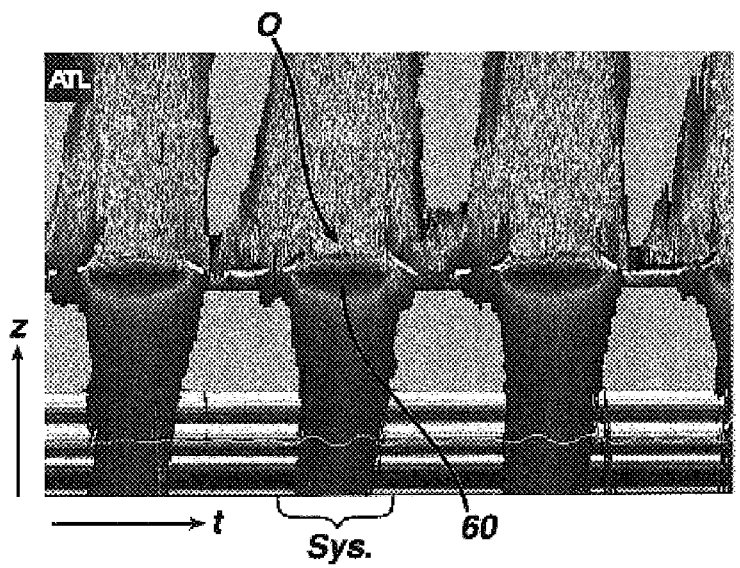
FIG. 4 illustrates a typical color M-mode display acquired along the M-line of FIG. 3.

In accordance with the principles of the present invention the flow rate through the orifice O is measured by acquiring color M-mode data from an M-line location 110 which is aligned with the jet 102. It is thus not necessary to know the exact location of the orifice O, but only to visualize the jet 102 in the ultrasound image, then place the M-line in alignment with the jet. Such an alignment is illustrated in FIG. 3. The resulting color M-mode image is produce by acquiring Doppler data from along the M-line location at a relatively high rate of acquisition. The time required to acquire a colorflow image of the heart chambers and mitral valve can be quite substantial, as B mode data must be acquired to image the heart structure, then each image line must be sampled numerous times to acquire the colorflow Doppler data. Thus, colorflow frame rates may be in the range of 10–20 frames per second, depending on image depth and sector width, or slower. The M-line is sampled at a much higher rate in a time-interleaved manner with a concurrently displayed two dimensional (2D) heart image; Doppler data from along the line can be acquired 500–1000 times per second, for instance. Thus, the flow through the regurgitant valve is sampled at a high temporal resolution each heart cycle, a rate of acquisition which is virtually certain to capture the flow data at the moment of peak regurgitation. A typical color M-mode display from such high speed acquisition is shown in FIG. 4, where each color M-line is oriented vertically in the depth (Z) dimension and successive M-lines are displayed in parallel in the time (t) dimension. A systolic phase of the heart cycle is bracketed at the bottom of the display and is seen to contain a distinctively colored region 60 where Doppler aliasing has occurred in the FCR region below the orifice O.

The flow rate through the orifice O is computed by measuring the distance d across the aliased region 60, and the velocities on either side of the region for a particular M-line. The opposite sides of the region 60 mark iso-velocity boundaries within the FCR. The radial distance r is computed from the equation $$Q_t = 2\pi r^2 v_2 = 2\pi (r+d)^2 v_1$$

for a given M-line in the color M-mode display during regurgitation, where $Q_t$ is the instantaneous flow rate, $v_2$ is the velocity at the second iso-velocity line 108 which is a radial distance r from the orifice O, and $v_1$ is the velocity at the outermost iso-velocity line 106 which is a radial distance of r+d from the orifice. The integral of these calculations for the systolic M-lines during which regurgitation occurs gives the regurgitant flow volume over the entire regurgitation. The effective orifice area (EOA) is then calculated by measuring the instantaneous velocity $V_t$ at the orifice at corresponding times during regurgitation using spectral Doppler, then computing $$EOA = Q_t / V_t$$

Figure 5:
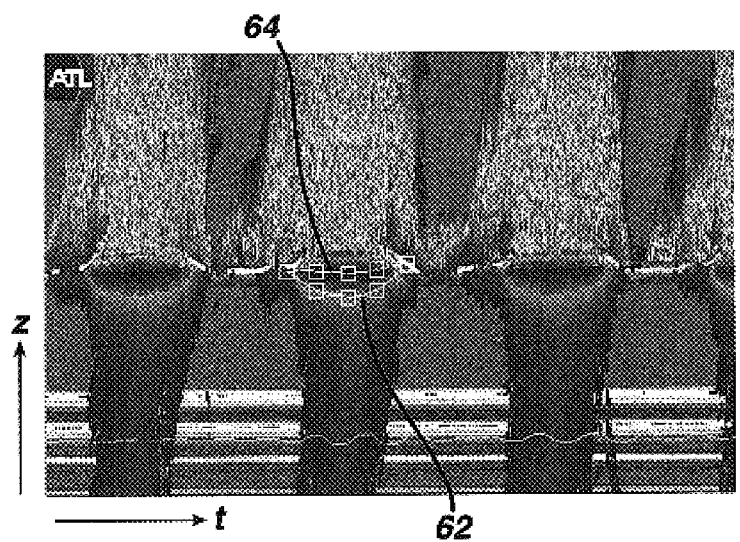
FIG. 5 illustrates the placement of an adjustable contour graphic over the FCR of the color M-mode display.

Several techniques may be used to measure the distance d across and the velocities $v_1$ and $v_2$ on either side of the aliasing region 60. One is to use a graphic consisting of two contour lines 62 and 64 which can be placed on the FCR region of the color M-mode display as shown in FIG. 5. The illustrated graphic has control points located on the lines as delineated by the small boxes in the drawing. The graphic can be moved and reshaped by pulling on the control points with a graphic pointing device such as a mouse until the contour lines 62 and 64 match the outline of the FCR region 60. A second and more preferable technique is to use automatic border drawing (ABD) to automatically trace the FCR region 60, such as one of the techniques discussed in U.S. patent 6,491,636. Once the border of the FCR region has been manually or automatically delineated, the ultrasound system can calculate the instantaneous flow rate $Q_t$, total volume flow $$\int_{t=0}^{T} Q_t,$$

and effective orifice area EOA automatically.

Figure 6:
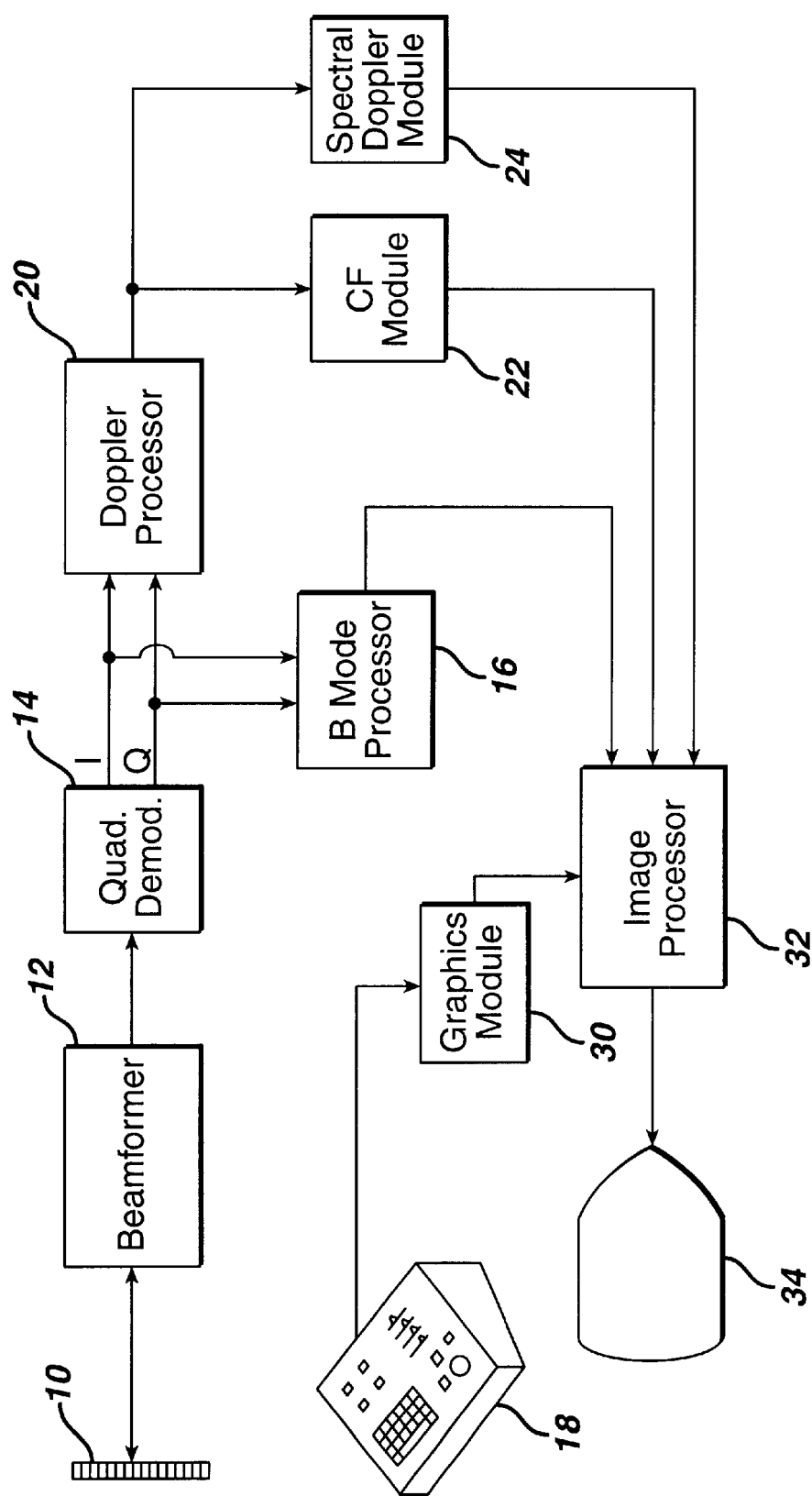
FIG. 6 illustrates an ultrasound system constructed in accordance with the principles of the present invention.

An ultrasound system constructed in accordance with the principles of the present invention is shown in FIG. 6. An array transducer 10 of a TEE probe is operated by a beamformer 12 to transmit ultrasonic beams over a region of the heart and acquires ultrasonic echo information. The echoes received by the beamformer for each beam and Doppler ensemble are demodulated by a quadrature demodulator 14 and the I and Q samples are B mode processed by a B mode processor 16 when forming a structural image of the tissue of the heart, and are Doppler processed by a Doppler processor 20 for flow presentation. The Doppler signals are processed for combining with the B mode image in a colorflow display by a CF module 22, and are processed for a spectral Doppler display by a spectral Doppler module 24. The B mode image data, the colorflow image data, and the spectral Doppler image data are all coupled to an image processor 32 where they are arranged and formatted for the desired image display. The resulting images are displayed on a display 34. Preferably the image processor 32 and display 34 function to display a colorflow ultrasound image, a color M-mode display, and a spectral Doppler display simultaneously. Such a three-image display enables the clinician to monitor all of the critical parameters of the diagnostic procedure at the same time. Also coupled to the image processor 32 is a graphics module 30, which is responsive to a user control 18 to locate graphics on the ultrasound images, such as the M-line which is placed over the colorflow image to define the color M-mode acquisition location, and the graphic tracing tool which is used to delineate the FCR region in the color M-mode display.

The ultrasound system of FIG. 6 may be used to quantify mitral valve regurgitation as follows. First, colorflow imaging is performed to image the suspect valve until a regurgitant jet and FCR are seen in the image. The color gain is adjusted so that an appropriate amount of color is seen in the heart chambers; if the gain is set too low, the image will lack necessary sensitivity, and if the gain is set too high there will be too much color blooming. The velocity scale (Doppler Nyquist limit) is adjusted until the FCR region is distinctively seen. This is easily done using the color bar 120 as shown in FIG. 3. In the exemplary color bar shown, the maximum velocity +V in the color display will be shown in yellow (Y). The maximum velocity −V in the opposite direction is shown in light blue (LB), and flow areas of zero velocity are shown in black (BK). Region of slow flow in the "+" direction are shown in dark red (DR), and regions of slow flow in the "−" direction are shown in dark blue (DB). If the velocity scale is set too high, the aliasing lines in the FCR region will be indistinguishable. If the velocity scale is set too low, the wall filter in the Doppler processor will cut off the Doppler data. When the velocity range is properly scaled, the aliasing lines in this example will appear as follows. Areas outside and below the iso-velocity boundary 106 will appear in dark red, and will transition to yellow at the outermost aliasing line 106. At the location of the line 106 the color will alias from +V to −V and will suddenly change from yellow to light blue. Above the iso-velocity boundary 106 the color will transition to dark blue, and at the second aliasing line 108 will undergo a sudden transition to black. This means that at boundary 106 the velocity magnitude is equal to |V|, and at boundary 108 the velocity magnitude is equal to |2| when no baseline shift is applied.

When these boundaries are separate and distinct in the image the clinician uses the control 18 to place the color M-mode cursor 110 over the jet in the colorflow image as shown in FIG. 3, and then begins to produce a color M-mode display as shown in FIG. 4. With the FCR region distinctly seen in both images, the clinician freezes the color M-mode display and manipulates the user control to draw or trace the border of the FCR region 60 with the contour lines 62,64 as shown in FIG. 5. When the contour lines are in the desired location around the region 60, the ultrasound system can compute and display the volume flow of the regurgitation calculated as described above from the measured values d, $v_1$, and $v_2$. Preferably the volume flow is continuously displayed and updated as the clinician refines the placement of the contour lines 62,64 on the color M-mode display. Also, the instantaneous volume flow rate measurements $Q_t$ (expressed in cm$^3$/sec) for each M-line of the color M-mode display during regurgitation can be plotted as a function of time to produce a volume flow rate curve. Integrating the area under the curve produces the total volume flow during regurgitation. Spectral Doppler measurements $V_t$ of the flow velocity (expressed in cm/sec) in the orifice area are produced for the same points in time as $Q_t$, preferably by the CW Doppler technique, and the quotient of $Q_t/V_t$ at the time of the peak velocity produces a measure of the effective area of the orifice when regurgitation is at its peak and the orifice is generally at its largest. Estimation of the EOA over the full interval of regurgitation provides a profile of the dynamic behavior of the orifice as the event transpires. In a constructed embodiment the flow rate curve and spectral Doppler spectrum are displayed simultaneously with synchronized pointers located on the time axis of each display. As the clinician moves the pointer along the time axis of one display, the pointer on the other display tracks to the same time location. A numerical calculation of EOA is displayed for the values of $Q_t$ and $V_t$ indicated by the instantaneous positions of the two pointers. Thus, the user can see and assess the size of the regurgitant orifice for any displayed flow rate or velocity during regurgitation.

What is claimed is:

1. A method of ultrasonically assessing valve regurgitation in the cardiovascular system comprising:
   acquiring ultrasonic images at a given frame rate of a region of a body which includes a valve;
   identifying a suspected regurgitant valve in one of the images;
   locating a cursor in the image which is located on a line extending through the suspected regurgitant valve;
   acquiring velocity information along the line at a repetition rate which is greater than the given frame rate; and
   utilizing the velocity information to estimate regurgitant flow through the suspected valve.

2. The method of claim 1, wherein acquiring comprises acquiring velocity information by the Doppler technique from points on the line.

3. The method of claim 2, wherein the line comprises an M-line, and wherein acquiring comprises acquiring color Doppler M-mode information from along the M-line.

4. The method of claim 1, wherein identifying comprises identifying a regurgitant jet in the vicinity of the suspected valve in an ultrasound image.

5. The method of claim 4, wherein acquiring further comprises aligning the cursor with the regurgitant jet in the ultrasound image.

6. The method of claim 5, wherein the cursor comprises an M-line, and wherein acquiring comprises acquiring color Doppler M-mode information from along the M-line location.

7. The method of claim 1, wherein the suspected regurgitant valve is characterized by a flow convergence region in the vicinity of the valve; and wherein acquiring comprises acquiring velocity information from two iso-velocity boundaries of the flow convergence region.

8. The method of claim 7, wherein utilizing comprises utilizing the velocity information from the two iso-velocity boundaries to calculate flow rate during valve regurgitation.

9. The method of claim 8, further comprising measuring the Doppler velocity of flow in the vicinity of the suspected valve during regurgitation; and wherein utilizing further comprises utilizing the calculated flow rate and measured Doppler velocity to estimate the size of a regurgitant orifice.

10. The method of claim 7, wherein acquiring further comprises imaging the flow convergence region by the Doppler M-mode technique; and tracing iso-velocity boundaries in the imaged flow convergence region.

11. The method of claim 10, wherein tracing comprises tracing the iso-velocity boundaries with a manually controlled graphic tracing tool.

12. The method of claim 10, wherein tracing comprises tracing the iso-velocity boundaries by automatic border drawing.

13. The method of claim 1, wherein identifying comprises visualizing the suspected valve in a two dimensional ultrasound image; and wherein acquiring comprises acquiring Doppler velocity information from along a line extending through the region of regurgitant flow in the two dimensional image.

14. The method of claim 13, wherein the line comprises an M-line, and wherein acquiring comprises acquiring color Doppler M-mode information from along the M-line location.

15. The method of claim 14, wherein the two dimensional image is a colorflow Doppler image.

16. A method of ultrasonically assessing valve regurgitation in the cardiovascular system comprising:
   displaying on a display a colorflow Doppler image of a suspected regurgitant valve in which the plane of the valve is approximately normal to the plane of the display;
   displaying in the image an M-line directed through the valve; and
   simultaneously displaying a Doppler M-mode display acquired from the M-line located in the colorflow Doppler image.

17. The method of claim 16, wherein the M-line is located in the region of suspected regurgitation in the colorflow Doppler image.

18. The method of claim 17, further comprising utilizing the data of the Doppler M-mode display to estimate regurgitant flow rate; and displaying an estimate of regurgitant flow rate.

19. A method of ultrasonically assessing valve regurgitation in the cardiovascular system comprising:

acquiring velocity information from the vicinity of a suspected regurgitant valve by the Doppler M-mode technique;

utilizing the velocity information to display regurgitant volume flow rate as a function of time during a given cardiac cycle; and displaying regurgitant flow velocity as a function of time during the given cardiac cycle.

20. The method of claim 19, further comprising utilizing time-aligned regurgitant volume flow rate data and regurgitant flow velocity data to estimate the size of a regurgitant orifice.

21. The method of claim 19, further comprising aggregating regurgitant volume flow rate data over a cardiac cycle to estimate total volume flow during a regurgitation event.

22. A method of ultrasonically assessing valve regurgitation in the cardiovascular system comprising:

identifying a suspected regurgitant valve in a colorflow Doppler image;

acquiring Doppler M-mode information from the region of the suspected regurgitant valve; and utilizing the Doppler M-mode information to estimate regurgitant flow through the suspected valve.

23. The method of claim 22, wherein identifying further comprises adjusting a colorflow Doppler parameter so that a flow convergence region in the vicinity of the suspected regurgitant valve is delineated in the image.

24. The method of claim 23, wherein the colorflow Doppler parameter is the velocity scale.

25. The method of claim 24 wherein adjusting comprises adjusting the velocity scale so that at least two aliasing boundaries are seen in the flow convergence region.

26. The method of claim 25 wherein acquiring further comprises acquiring velocity measurements at the aliasing boundaries; and wherein utilizing comprises utilizing the velocity measurements to estimate volume flow through the valve during regurgitation.

27. The method of claim 26, wherein utilizing further comprises utilizing estimated volume flow to estimate the size of a valve orifice during regurgitation.

* * * * *